United States Patent [19]

Iwataki et al.

[11] 4,431,814
[45] Feb. 14, 1984

[54] HETEROCYCLIC COMPOUNDS

[75] Inventors: Isao Iwataki; Minoru Kaeriyama; Nobuo Matsui; Tomio Yamada, all of Kanagawa, Japan

[73] Assignee: Nippon Soda Company Limited, Tokyo, Japan

[21] Appl. No.: 348,757

[22] Filed: Feb. 16, 1982

Related U.S. Application Data

[62] Division of Ser. No. 187,412, Sep. 15, 1980, abandoned.

[30] Foreign Application Priority Data

Oct. 3, 1979 [JP] Japan .................. 54-127707
Apr. 18, 1980 [JP] Japan .................. 55-50363

[51] Int. Cl.³ .................. C07D 263/26; A61K 31/42
[52] U.S. Cl. .................. 548/230; 548/183; 548/229; 424/270; 424/272; 424/263; 546/209
[58] Field of Search ............. 548/229, 230; 424/272

[56] References Cited

U.S. PATENT DOCUMENTS

| | | | |
|---|---|---|---|
| 3,119,833 | 1/1964 | Sovish | 548/230 |
| 3,193,559 | 7/1965 | Regnier et al. | 548/230 |
| 3,754,000 | 8/1973 | Fauran et al. | 548/229 |
| 4,186,129 | 1/1980 | Huth et al. | 548/186 |

FOREIGN PATENT DOCUMENTS

| | | | |
|---|---|---|---|
| 48-11018 | 4/1973 | Japan | 548/188 |
| 2059961 | 4/1981 | United Kingdom | 548/230 |

Primary Examiner—Mary C. Lee
Assistant Examiner—S. A. Gibson
Attorney, Agent, or Firm—George B. Oujevolk

[57] ABSTRACT

A compound of the formula

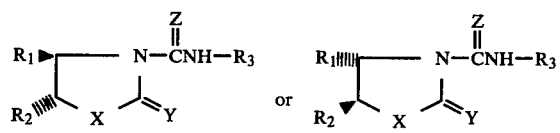

wherein typical representations of X, Y and Z is oxygen or sulfur; $R_1$ is methyl; $R_2$ is phenyl substituted with chlor, methyl, methoxy, nitro or methylenedioxy; and $R_3$ is cyclohexyl, methylcyclohexyl or tetrahydropyranyl, is useful as an acaricide.

15 Claims, No Drawings

HETEROCYCLIC COMPOUNDS

This is a division of application Ser. No. 187,412 filed Sept. 15, 1980, now abandoned.

DESCRIPTION

The present invention relates to a novel heterocyclic compound, acaricidal compositions in the form of mixtures of such compounds with carrier vehicles, and methods for producing such compounds and for using such compounds for controlling acarids.

Some derivatives having oxazolidone or thiazolidone skeletons are known as herbicides or anticonvulsants, and there are descriptions, for instance, in U.S. Pat. No. 3,247,219 and JACS 73,95 (1951) on 3-carbamoyloxazolidone derivatives, and in U.S. Pat. No. 3,491,108 on thiazolidone derivatives.

The present invention provides a compound having the formula

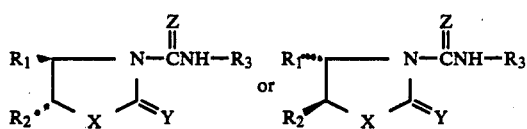

wherein X, Y and Z is oxygen or sulfur; $R_1$ is alkyl of one to four carbon atoms; $R_2$ is five membered heterocycle having oxygen or sulfur, phenyl, substituted phenyl having one or two substituent alkyl, halogen, haloalkyl, alkoxy, nitro or methylenedioxy; and $R_3$ is five to seven membered cycloalkyl, cycloalkenyl, or heterocycle having oxygen, sulfur, or nitrogen, being in each case with or without substituent.

The compounds of the formula (I) exhibit strong acaricidal properties.

The present invention further provides processes for the production of the compound of the formula (I) the process being described as follows:

(a) The compound of the formula

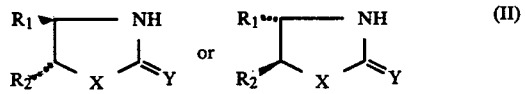

wherein $R_1$, $R_2$, X and Y have the above meanings, is reacted with the isocyanate or isothiocyanate of the formula $$R_3NCZ \quad (III)$$

wherein $R_3$ and Z have the above meanings.

The starting material indicated by the formula (II) can be prepared, for example, as illustrated by the following equations:

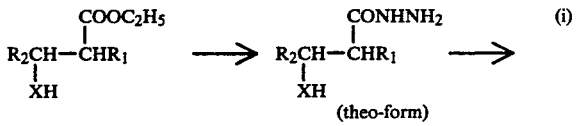

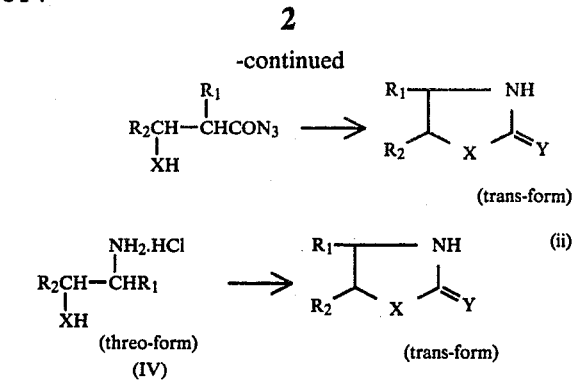

The compound of the formula (II) is dissolved in an inert organic solvent such as toluene, tetrahydrofuran and dimethylsulfoxide, and to the solution are added the compound of the formula (III) and a catalyst, for instance, such a basic compound as 1,8-diazabicyclo(5, 4, 0) undecene-7 (DBU), sodium hydride and tertiary amines, or a Lewis acid such as stannous chloride, boron trifluoride and zinc chloride. The reaction is usually carried out at 0° C. to room temperature under stirring for a period of one to several hours. After the reaction is completed, the reaction mixture is poured into water, and the product is separated by filtration or solvent extraction.

(b) The compound of the formula

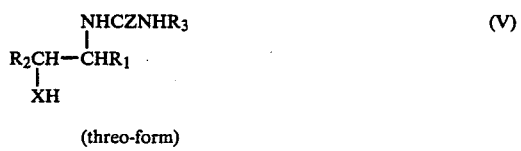

wherein $R_1$, $R_2$, $R_3$, X and Z have the above meanings, is reacted with a carbonylating or thiocarbonylating reagent in the presence of an acid-binding reagent. The starting material indicated by the formula (V) can be prepared, for example, by reacting the compound represented by the formula (III) with the compound represented by the formula (IV). As the carbonylating or thiocarbonylating reagent, such conventional reagents as potassium carbonate, phosgene, thiophosgene, trichloromethyl chloroformate are suitable. For the acid-binding reagent, amines such as dimethylaniline or triethylamine and other basic compounds are employed. The compound of the formula (V) and the acid-binding reagent are dissolved in an inert organic solvent such as benzene, chloroform and ethylacetate, and to the solution is added the carbonylating or thiocarbonylating reagent. The reaction is usually conducted at 0° C. to room temperature for a period of one to several hours. After the reaction is completed, the basic material in the reaction mixture is removed by washing the mixture with dilute hydrochloric acid or water, and thereafter it is worked up to obtain the product in accordance with usual procedures.

In the novel compounds of the invention, two substituents $R_1$ and $R_2$ on the heterocyclic ring are trans disposition, as shown in the formula (I). In case $R_3$ is a certain substituted cyclohexyl or tetrahydropyranyl ring, other isomer configurations present in the carbamoyl moiety, however, all the isomers thus formed are also within the scope of this invention.

The manner in which the compound of the present invention can be prepared is illustrated, without limitation, by the following examples.

EXAMPLE 1

Trans-3-cyclohexylcarbamoyl-4-methyl-5-(4-methylphenyl)-2-oxazolidone

Into 30 ml of dimethylsulfoxide was dissolved 3.8 g of trans-4-methyl-5-(4-methylphenyl)-2-oxazolidone, and to the solution was added with ice-cooling 2.7 g of cyclohexylisocyanate and one drop of DBU. The mixture was warmed gradually to room temperature with stirring, and the reaction was continued for 1 hour. The reaction mixture was poured into water, and extracted with ethylacetate. The ethylacetate layer was dried, the solvent was evaporated and the residue was recrystallized from ligroin. The yield of the desired product was 4.7 g.

EXAMPLE 2

Trans-4-methyl-5-(4-methylphenyl)-3-(2-tetrahydropyranylcarbamoyl)-2-oxazolidone Into 20 ml of dimethylsulfoxide was dissolved 1.5 g of trans-4-methyl-5-(4-methylphenyl)-2-oxazolidone, and to the solution were added with ice-cooling 0.9 g of 2-tetrahydropyranyl isocyanate and one drop of DBU. The mixture was stirred for one hour at room temperature. The reaction mixture was poured into water, and extracted with ethylacetate. The ethylacetate layer was dried, the solvent was evaporated and the oily residue was purified with a column chromatography. The yield of the desired product was 0.7 g.

EXAMPLE 3

Trans-3-cyclohexylcarbamoyl-4-methyl-5-(2-thienyl)-2-oxazolidone

Into 10 ml of dimethylsulfoxide were dissolved 2 g of trans-4-methyl-5-thienyl-2-oxazolidone and 1.4 g of cyclohexylisocyanate, and then 1 g of DBU was added to the solution at room temperature. After the mixture was stirred for two hours, the reaction mixture was poured into ice-cold water, the deposited crystals were filtered and dried. The yield of the desired product was 2.8 g.

EXAMPLE 4

Trans-3-cyclohexylcarbamoyl-4-methyl-5-(4-methylphenyl)-2-oxazolidone

Into 100 ml ethylacetate were dissolved 2 g of 1-cyclohexyl-3-[1-hydroxy-1-(4-methylphenyl)-2-propyl] urea and 1.6 g of N, N-dimethylaniline, and to the solution was added with stirring at 5° C. to 10° C. 1 g of trichloromethylchloroformate dissolved in 10 ml of ethylacetate. After the mixture was stirred for one hour at the temperature, the reaction mixture was washed with a 5% hydrochloric acid and water, the washed mixture was dried and the solvent was evaporated. The yield of the desired product was 1.7 g.

EXAMPLE 5

Trans-4-methyl-5-(4-methylphenyl)-3-(2-tetrahydropyranylcarbamoyl)oxazolidine-2-thione Into 10 ml of ethylacetate were dissolved 1.2 g of 1-(2-tetrahydropyranyl)-3-[threo-2-hydroxy-1-(4-methylphenyl)-2-phenyl] urea and 1.0 g of N, N-dimethylaniline, and to the solution was added with stirring at 0° C. 0.7 g of thiophosgene dissolved in 5 ml of ethylacetate. After the mixture was stirred for 3 hours at 0° C., the reaction mixture was poured into a 5% hydrochloric acid, and extracted with ethylacetate. The ethylacetate layer was dried, the solvent was evaporated and the oily residue was purified with a column chromatography. The yield of the desired product was 0.5 g.

EXAMPLE 6

Trans-4-methyl-5-(4-methylphenyl)-3-cyclohexylcarbamoyl-2-thiazolidone

Into 50 ml of ethylacetate were dissolved 4.8 g of 1-cyclohexyl-3-[threo-1-mercapto-1-(4-methylphenyl)-2-propyl] urea and 3.8 g of N, N-dimethylaniline, and to the solution was added with stirring 2.5 g of trichloromethyl chloroformate dissolved in 10 ml of ethylacetate. After the mixture was stirred for four hours at room temperature, the reaction mixture was washed with a 5% hydrochloric acid and water, the washed mixture was dried and the solvent was evaporated. The oily residue was purified with a column chromatography. The yield of the desired product was 3.4 g.

EXAMPLE 7

Trans-4-methyl-5-(4-chlorophenyl)-3-cyclohexylcarbamoyl-2-thiazolidone

Into 10 ml of dimethylsulfoxide were dissolved 2 g of trans-4-methyl-5-(4-chlorophenyl)-2-thiazolidone and several drops of DBU, and to the solution was added dropwise 1.2 g of cyclohexyl isocyanate with cooling. After the mixture was stirred for 3 hours at room temperature, the reaction mixture was poured into ice-water and extracted with chloroform. The chloroform layer was washed with water, dried, and the solvend was evaporated. The oily residue was purified with a column chloromatography. The yield of the desired product was 2.6 g.

EXAMPLE 8

Trans-4-methyl-5-(4-methylphenyl)-3-(trans-2-methylcyclohexylcarbamoyl)-2-thiazolidone Into 60 ml of benzene was dissolved 3 g of trans-4-methyl-5-(4-methylphenyl)-2-nitrosoamino-2-thiazoline, and to the solution were added at room temperature 2 g of trans-2-methylcyclohexyl isocyanate and several drops of triethylamine. After the mixture was stirred for one hour at room temperature, the reaction was continued for further 3 hours under heating and reflux. The reaction mixture was washed with water, dried and the solvent was evaporated. The oily residue was purified with a column chromatography. The yield of the desired product was 1.8 g.

Inclusive of the above, compounds within the scope of this invention which can be prepared in an analogeous manner are tabulated in Table 1.

TABLE 1

$$\underset{R_2}{\overset{R_1}{\diagdown}}\diagup\underset{X}{\overset{}{\diagdown}}\underset{Y}{\overset{N-\overset{Z}{\overset{\|}{C}}NH-R_3}{\diagup}}$$

| Compound No. | X | Y | Z | $R_1$ | $R_2$ | $R_3$ | Physial Properties [m.p.] °C. Racemate |
|---|---|---|---|---|---|---|---|
| 1 | O | O | O | $CH_3$ | 4-$CH_3$-phenyl | cyclohexyl (H) | [98–100] |
| 2 | " | " | " | " | 3-$CH_3$-phenyl | " | $n_D^{29}$ 1.5330 |
| 3 | " | " | " | " | 2-$CH_3$-phenyl | " | [64–65] |
| 4 | " | " | " | " | phenyl | " | [85–86.5] |
| 5 | " | " | " | " | 4-Cl-phenyl | " | [129–130] |
| 6 | " | " | " | " | 2-Cl-phenyl | " | [105–107] |
| 7 | " | " | " | " | 2,4-di-Cl-phenyl | " | [80–82] |
| 8 | " | " | " | " | 4-Br-phenyl | " | [126–128] |
| 9 | " | " | " | $C_2H_5$ | 4-$CH_3$-phenyl | " | $n_D^{30.5}$ 1.5268 |
| 10 | " | " | " | $CH_3$ | 2,4-di-$CH_3$-phenyl | " | [66–68] |
| 11 | " | " | " | " | 3,5-di-$CH_3$-phenyl | " | [70–72] |

TABLE 1-continued

| Compound No. | X | Y | Z | R₁ | R₂ | R₃ | Physical Properties [m.p.] °C. Racemate |
|---|---|---|---|---|---|---|---|
| 12 | " | " | S | " | 4-CH₃-C₆H₄- | " | [115-116] |
| 13 | " | " | O | " | 4-$^t$C₄H₉-C₆H₄- | " | [105-107] |
| 14 | " | " | " | " | 4-$^i$C₃H₇-C₆H₄- | " | [76-78] |
| 15 | " | " | " | " | 4-CH₃O-C₆H₄- | " | [76-78] |
| 16 | " | " | " | " | 4-CH₃-C₆H₄- | tetrahydropyran-2-yl | [94.5-96] |
| 17 | " | " | " | " | 3,4-Cl₂-C₆H₃- | cyclohexyl | [160-162] |
| 18 | " | " | " | " | 4-CH₃-C₆H₄- | cyclopentyl | [71-72] |
| 19 | " | " | " | " | " | cycloheptyl | [61-62] |
| 20 | " | S | " | " | 4-$^t$C₄H₉-C₆H₄- | cyclohexyl | [87-89] |
| 21 | " | O | " | " | 4-$^n$C₁₂H₂₅-C₆H₄- | " | [50-52] |
| 22 | " | " | " | " | 3,4-(CH₃O)₂-C₆H₃- | " | [127-128.5] |
| 23 | " | " | " | " | 4-CF₃-C₆H₄- | | [152-154] |

TABLE 1-continued $$R_1 \overset{\displaystyle R_2}{\underset{\displaystyle X}{\diagdown}} \overset{\displaystyle Z}{\underset{\displaystyle Y}{\diagup}} N - \overset{\displaystyle Z}{\underset{\displaystyle}{C}} NH - R_3 \qquad R_1 \overset{\displaystyle R_2}{\underset{\displaystyle X}{\diagdown}} \overset{\displaystyle Z}{\underset{\displaystyle Y}{\diagup}} N - \overset{\displaystyle Z}{\underset{\displaystyle}{C}} NH - R_3$$

| Compound No. | X | Y | Z | $R_1$ | $R_2$ | $R_3$ | Physical Properties [m.p.] °C. Racemate |
|---|---|---|---|---|---|---|---|
| 24 | " | " | " | " | 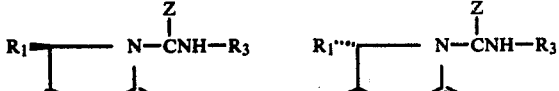 | " | [74-76] |
| 25 | " | S | " | " | 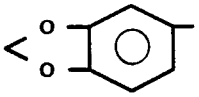 | " | $n_D^{28}$ 1.5739 |
| 26 | " | O | " | " | 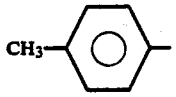 | " | $n_D^{26}$ 1.5339 |
| 27 | " | " | " | " | 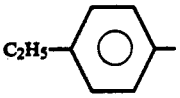 | " | [89-90.5] |
| 28 | " | " | " | " | 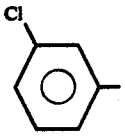 | " | [78.5-80] |
| 29 | " | " | " | " | 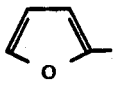 | " | [45-47] |
| 30 | " | " | " | " | 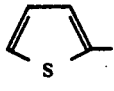 | 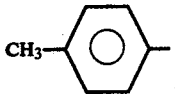  (N/CH₃ Cis: trans = 60:40)* | $n_D^{27}$ 1.5331 |
| 31 | " | " | " | " | " | 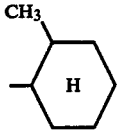 (N/CH₃: trans) | [51-59] |
| 32 | " | " | " | " | " | 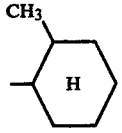 (N/CH₃: cis) | [109-120] |
| 33 | " | " | " | " | " | 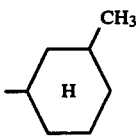 (N/CH₃: cis/trans = 7/3) | $n_D^{20}$ 1.5361 |

TABLE 1-continued

| Compound No. | X | Y | Z | R₁ | R₂ | R₃ | Physical Properties [m.p.] °C. Racemate |
|---|---|---|---|---|---|---|---|
| 34 | " | " | " | " | " | 4-methylcyclohexyl (N/CH₃ = trans) | [112–118] |
| 35 | " | " | " | " | " | 2,6-dimethylcyclohexyl | [116–122] |
| 36 | " | " | " | " | " | cyclohex-3-enyl | [95–96] |
| 37 | " | " | " | " | 3,4-methylenedioxyphenyl | tetrahydropyran-2-yl | [127–129] |
| 38 | S | S | " | " | 4-methylphenyl | cyclohexyl | [96–97] |
| 39 | O | O | S | " | phenyl | " | [93–95] |
| 40 | S | " | O | " | 4-methylphenyl | " | [86–87] |
| 41 | O | S | " | " | " | tetrahydropyran-2-yl | $n_D^{20.5}$ 1.5800 |
| 42 | " | " | " | " | 4-chlorophenyl | cyclohexyl | [89–91] |
| 43 | " | O | S | " | 2,3-dimethylphenyl | " | [90–92] |
| 44 | " | " | O | " | 2,3-dimethylphenyl | tetrahydropyran-2-yl | [88–90] |

TABLE 1-continued
| Compound No. | X | Y | Z | R₁ | R₂ | R₃ | Physical Properties [m.p.] °C. Racemate |
|---|---|---|---|---|---|---|---|
| 45 | " | " | " | " | 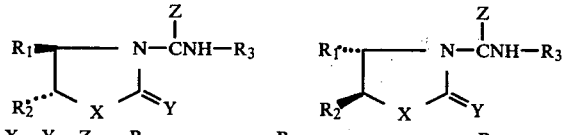 | " | [75–76] |
| 46 | " | " | " | " | 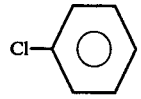 | 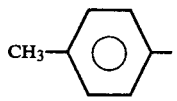 | [109–111] |
| 47 | " | " | " | " | 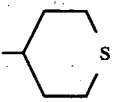 | 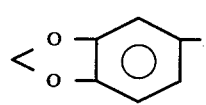<br>(N/CH₃: trans) | $n_D^{17.2}$ 1.5460 |
| 48 | " | " | " | " | 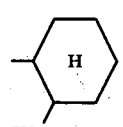 | 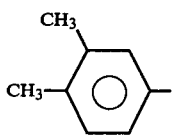 | $n_D^{17.8}$ 1.5376 |
| 49 | " | " | " | " | 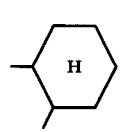 | 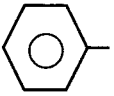 | $n_D^{19.3}$ 1.5395 |
| 50 | " | " | " | " | 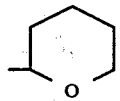 | 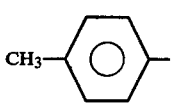 | [95–97] |
| 51 | " | " | " | " | " | 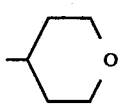 | [85–104] |
| 52 | " | " | " | " | " | 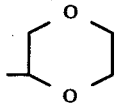 | [78–80] |
| 53 | " | " | " | " | " | 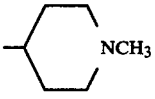 | $n_D^{20.5}$ 1.5603 |
| 54 | " | " | " | " | 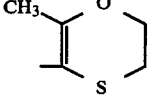 | 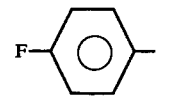 | [122–123] |
| 55 | S | " | " | " | 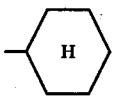 | " | [93–96] |

TABLE 1-continued $$\underset{R_2}{\overset{R_1}{\diagdown}}\overset{}{\underset{X}{\diagup}}\overset{\overset{Z}{\|}}{\underset{Y}{\overset{N-CNH-R_3}{\diagdown}}}\quad\underset{R_2}{\overset{R_1\cdots}{\diagdown}}\overset{}{\underset{X}{\diagup}}\overset{\overset{Z}{\|}}{\underset{Y}{\overset{N-CNH-R_3}{\diagdown}}}$$

| Compound No. | X | Y | Z | R₁ | R₂ | R₃ | Physical Properties [m.p.] °C. Racemate |
|---|---|---|---|---|---|---|---|
| 56 | " | " | " | " | 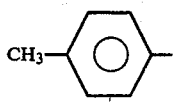 CH₃— | 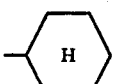 H, CH₃ (N/CH₃: trans) | [86.5–98] |
| 57 | " | " | " | " | " | 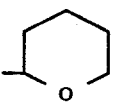 O | $n_D^{27}$ 1.5638 |
| 58 | " | " | " | " | 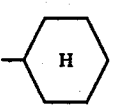 Cl— | H | [93–96] |
| 59 | " | " | " | " | 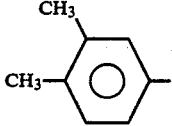 CH₃, CH₃ | " | [84–85] |
| 60 | " | " | " | " | 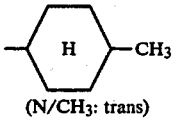 CH₃— | 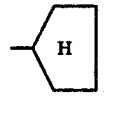 H, CH₃ (N/CH₃: trans) | [147–149] |
| 61 | " | " | " | " | " | 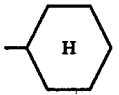 H | [96–101] |
| 62 | " | " | " | " | 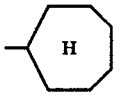 ᵗC₄H₉— | H | [125–128] |
| 63 | " | " | " | " | 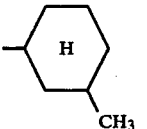 CH₃— | H | [76–77] |
| 64 | " | " | " | " | " | 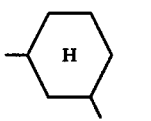 H, CH₃ | $n_D^{26.5}$ 1.5577 |
| 65 | " | " | " | " | " | H, CH₃ (N/CH₃: cis) | [72.5–74.5] |
| 66 | " | " | S | " | " | 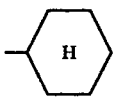 H | [94.5–97] |

TABLE 1-continued

| Compound No. | X | Y | Z | R₁ | R₂ | R₃ | Physical Properties [m.p.] °C. Racemate |
|---|---|---|---|---|---|---|---|
| 67 | " | " | O | " | " | 2,6-dimethylcyclohexyl | $n_D^{28.0}$ 1.5532 |
| 68 | " | " | " | " | 4-methylphenyl | cyclohexyl-H | $n_D^{30.0}$ 1.5657 |
| 69 | " | " | " | " | 2-methylphenyl | " | [116–117.5] |
| 70 | " | " | " | " | 4-ethylphenyl | " | [85.5–88] |
| 71 | " | " | " | " | 4-n-C₁₂H₂₅-phenyl | cyclohexyl-H | [46–49] |
| 72 | " | " | " | " | 3,5-dimethylphenyl | " | [99–102.5] |
| 73 | " | " | " | " | 3-chlorophenyl | " | [77–79] |
| 74 | " | " | " | " | 2-chlorophenyl | " | [97–99] |
| 75 | " | " | " | " | 3,4-dichlorophenyl | " | [136–138] |
| 76 | " | " | " | " | 4-bromophenyl | " | [99–101] |

TABLE 1-continued

| Compound No. | X | Y | Z | R₁ | R₂ | R₃ | Physical Properties [m.p.] °C. Racemate |
|---|---|---|---|---|---|---|---|
| 77 | " | " | " | " | 4-F-phenyl | " | [90-91.5] |
| 78 | " | " | " | " | 4-CH₃O-phenyl | " | $n_D^{30.5}$ 1.5590 |
| 79 | " | " | " | " | 3,4-methylenedioxyphenyl | " | $n_D^{26}$ 1.5751 |
| 80 | " | " | S | " | 4-Cl-phenyl | " | [108-110] |
| 81 | " | " | O | " | " | 2-CH₃-cyclohexyl (N/CH₃: trans) | [116-121.5] |
| 82 | " | " | " | " | " | 2-CH₃-cyclohexyl (N/CH₃: cis) | [83-87] |
| 83 | " | " | " | " | " | 4-CH₃-cyclohexyl (N/CH₃: trans) | [149-153] |
| 84 | " | " | " | " | " | tetrahydropyran-2-yl | $n_D^{29}$ 1.5801 |
| 85 | " | " | " | " | " | tetrahydropyran-2-yl (Isomer) | $n_D^{29}$ 1.5760 |
| 86 | " | " | " | " | " | 2,6-di-CH₃-cyclohexyl | $n_D^{28.5}$ 1.5604 |
| 87 | " | " | " | " | 4-BrCH₂-phenyl | cyclohexyl | [106-108] |

TABLE 1-continued

| Compound No. | X | Y | Z | R₁ | R₂ | R₃ | Physical Properties [m.p.] °C. Racemate |
|---|---|---|---|---|---|---|---|
| 88 | " | " | " | " | 4-Cl-C₆H₄- | cyclopentyl (H) | [97–98] |
| 89 | " | " | " | " | 4-Cl-C₆H₄- | cycloheptyl (H) | [87–89] |
| 90 | " | " | " | " | 3-Cl-4-CH₃-C₆H₃- | cyclohexyl (H) | [120–121] |
| 91 | " | " | " | " | 2,4-(CH₃)₂-C₆H₃- | " | [95–91] |
| 92 | " | " | " | C₂H₅ | 4-CH₃-C₆H₄- | " | [113–115] |
| 93 | " | " | " | CH₃ | 4-ⁱC₃H₇-C₆H₄- | " | [120–123] |
| 94 | " | " | " | " | 4-Cl-C₆H₄- | cyclohexenyl | [83–85] |
| 95 | " | " | " | " | 4-CH₃-C₆H₄- | 1,4-dioxan-2-yl | $n_D^{27.5}$ 1.5679 |
| 96 | " | " | " | " | 4-Cl-C₆H₄- | " | $n_D^{25.5}$ 1.5803 |
| 97 | " | " | " | " | 4-CH₃-C₆H₄- | cyclohexenyl | [67–68] |
| 98 | " | " | " | " | 2-thienyl | cyclohexyl (H) | [133–137] |
| 99 | " | " | " | " | 4-CF₃-C₆H₄- | " | [133–135] |

TABLE 1-continued $$\underset{R_2^*}{\overset{R_1}{|}}\!\!-\!\!\underset{X}{\overset{Z}{\underset{|}{N}}}\!\!-\!\!\overset{}{\underset{Y}{\overset{\|}{C}}}NH\!-\!R_3 \qquad \underset{R_2^*}{\overset{R_1\cdots}{|}}\!\!-\!\!\underset{X}{\overset{Z}{\underset{|}{N}}}\!\!-\!\!\overset{}{\underset{Y}{\overset{\|}{C}}}NH\!-\!R_3$$

| Compound No. | X | Y | Z | $R_1$ | $R_2$ | $R_3$ | Physical Properties [m.p.] °C. Racemate |
|---|---|---|---|---|---|---|---|
| 100 | " | " | " | " | CH₃O–,CH₃O– phenyl | " | [117–119] |
| 101 | " | " | " | " | furyl (O) | " | [118.5–121.5] |
| 102 | " | " | " | $^iC_3H_7$ | CH₃–phenyl | " | $n_D^{30}$ 1.5886 |
| 103 | " | S | " | CH₃ | Cl–phenyl | " | [101–103] |
| 104 | " | O | " | " | NO₂–phenyl | " | [114–117] |
| 105 | O | " | " | " | BrCH₂–phenyl | " | [76–78] |
| 106 | " | " | " | " | Cl,CH₃–phenyl | H–cyclohexyl | [126–128] |
| 107 | " | " | " | " | CH₃,CH₃–phenyl | " | [66–68] |
| 108 | " | " | " | " | Cl,Cl–phenyl | " | [109–111] |

*Isomer configuration in carbamoyl moiety

As already mentioned, the compounds of this invention exhibit outstanding acaricidal properties, and they are especially useful for controlling eggs and larvae of acarids. Among the acarids which can be effectively controlled with the compounds are the two spotted spider mite, citrus red mite, and the like. The compounds may be used with success for the control of ticks. Furthermore, herbicidal usages are expected for a certain group of the compounds.

The compounds according to this invention are utilized, if desired, in a form of the usual acaricidal formulations with conventional diluents or extenders, and the formulations include wettable powders, granules, dusts, emulsifiable concentrates, flowable formulations, and the like. As solid carrier vehicles, such cereal flours as soy bean flour and wheat flour, such ground minerals as diatomaceous earth, apetite, gypsum, talc, pyrophyllite and clay are used. As liquid diluent carriers such inert organic liquids as kerosene, mineral oil, petroleum, solvent naphtha, xylene, cyclohexane, cyclohexanone, dimethylformamide, alcohol, and acetone, as well as water are employed. Conventional pesticidal surface-active agents including emulsifying agents and/or dispersing agents may be used when homogeneous and stable formulations are desired.

The concentration of the active ingredient in the acaricidal compositions may vary in accordance with types of the formulation, and it is settled generally at about 5 to 80 weight percent and preferably 20 to 80 weight percent for the wettable powders; 5 to 70 weight percent and preferably 10 to 50 weight percent for the emulsifiable concentrates; and 0.5 to 20 weight percent and prefeably 1 to 10 weight percent for the dust formulation.

Wettable powders, emulsifiable concentrates and flowable formulations thus formulated are usually diluted with water to form the suspensions or emulsions, which are applied by spraying or drenching. Dusts and granules are applied directly.

Non-limiting examples of the acaricidal composition of the invention are as mentioned below:

EXAMPLE 9

Emulsifiable Concentrate

| | |
|---|---|
| Compound of this invention | 10 parts by weight |
| Dimethylformamide | 50 parts by weight |
| Xylene | 35 parts by weight |
| Alkylarylpolyoxyethylene ether | 5 parts by weight |

These are mixed together to provide an emulsifiable concentrate. It is diluted with water to an emulsion of the desired concentration.

EXAMPLE 10

Wettable Powder

| | |
|---|---|
| Compound of this invention | 20 parts by weight |
| Diatomaceous earth | 70 parts by weight |
| White carbon | 5 parts by weight |
| Sodium alkylsulfate | 5 parts by weight |

These are mixed and ground to provide homogeneous powders. It is diluted with water to a suspension of the desired concentration.

EXAMPLE 11

Dust Formulation

| | |
|---|---|
| Compound of this invention | 1 parts by weight |
| Talc | 98.6 parts by weight |
| Silicone oil | 0.3 parts by weight |
| Alkylarylpolyoxyethylene ether | 0.1 parts by weight |

These are mixed and pulverized to provide homogeneous fine powders.

Use of the combinations of the compound of the present invention with other plant protection agents such as other acaricides, insecticides or herbicides may provide acaricidal and insecticidal compositions which achieve results unattainable with separate compositions of the individual component. Other components with which the compound of the present invention can be used are, for example, as follows:

Acaricides chlorfenethol, chlorobenzilate, chloropropylate, proclonol, phenisobromolate, dicofol, dinobuton, binapacryl, chlordimeform, amitraz, propargite, PPPS, benzoxamate, cyhexatin, fenlutatin oxide, polynactins, chinomethionate, thioquinox, chlorfenson, tetradifon, tetrasul, cycloprate, Kayacide, Kayahope, 3-n-dodecyl-1,4-naphthoquinone-2-yl acetate, Calcium polysulfide Insecticides (Organophosphorous compounds)

fenthion, fenitrothion, diazinon, chlorpyrifos, EPS, vamidothion, phenthoate, dimethoate, formothion, malathion, trichlorofon thiometon, phosmet, menazon, dichlorvos, acephate, EPBP, dialifor, methyl parathion, oxydemeton methyl, ethion, aldicarb, propoxur (Pyrethroids)

permethrin, cypermethrin, decamethrin, fenvalerate, fenpropathrin, pyrethrins, allethrins, tetramethrin, resmethrin, barthrin, dimethrin, propathrin, prothrin, 3-phenoxybenzyl-2, 2-dichloro-1-(4-ethoxyphenyl)-1-cyclopropancarboxylate, α-cyano-3-phenoxybenzyl-2, 2-dichloro-1-(4-ethoxyphenyl)-1-cyclopropanecarboxylate, (RS)-α-cycno-3-phenoxybenzyl(RS)-2-(4-trichloromethoxyphenyl)-3-methylbutylate, (RS)-α-cyano-3-phenoxybenzyl(RS)-2-(2-chloro-4-trichloromethylanilino)-3-methylbutylate.

The unexpected superiority and outstanding activity of the novel compounds of the present invention is illustrated, without limitation, by the following test:

Test 1

The primary leaves of kidney beans planted in pots were infested respectively with 30 adult females of the two-spotted spider mite. The leaves were sprayed until dew moist with an aqueous emulsion prepared with the emulsion concentrate of Example 9 and containing 500 ppm or 125 ppm of the active compound. After 3 days of the ovipositing period, mites which survived as well as killed were removed from the leaves. On the 11th day, the degree of destruction as a percentage of $$\frac{A-B}{A}$$

wherein A means the number of mites developed from eggs on untreated leaves and B means the number of mites developed from eggs on treated leaves. The result are as shown in the following Table 2.

TABLE 2

| | Degree of Destruction | |
|---|---|---|
| Compound No. | 500 ppm (%) | 125 ppm (%) |
| 1 | 100 | 100 |
| 2 | 100 | 99 |
| 4 | 100 | 100 |
| 5 | 100 | 97 |
| 8 | 100 | 95 |
| 9 | 95 | 84 |
| 10 | 100 | 100 |
| 11 | 100 | 85 |
| 12 | 98 | 98 |
| 14 | 100 | 95 |
| 16 | 100 | 100 |
| 19 | 100 | 100 |
| 21 | 100 | 100 |

TABLE 2-continued

| Compound No. | Degree of Destruction 500 ppm (%) | 125 ppm (%) |
| --- | --- | --- |
| 23 | 100 | 64 |
| 24 | 100 | 100 |
| 25 | 100 | 100 |
| 26 | 100 | 86 |
| 27 | 100 | 99 |
| 28 | 99 | 88 |
| 29 | 100 | 99 |
| 30 | 100 | 100 |
| 31 | 100 | 100 |
| 33 | 100 | 85 |
| 34 | 100 | 100 |
| 36 | 100 | 95 |
| 37 | 100 | 100 |
| 38 | 100 | 100 |
| 40 | 100 | 100 |
| 41 | 100 | 100 |
| 42 | 100 | 100 |
| 43 | 100 | 77 |
| 44 | 100 | 100 |
| 45 | 100 | 100 |
| 47 | 100 | 100 |
| 48 | 100 | 100 |
| 49 | 100 | 100 |
| 50 | 90 | 60 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 63 | 100 | 100 |
| 64 | 100 | 98 |
| 65 | 100 | 100 |
| 66 | 100 | 100 |
| 67 | 100 | 100 |
| 68 | 100 | 100 |
| 69 | 100 | 100 |
| 70 | 100 | 100 |
| 71 | 100 | 100 |
| 73 | 100 | 100 |
| 74 | 100 | 80 |
| 75 | 100 | 62 |
| 76 | 100 | 100 |
| 77 | 100 | 100 |
| 78 | 100 | 100 |
| 79 | 100 | 100 |
| 80 | 100 | 99 |
| 81 | 100 | 100 |
| 82 | 100 | 100 |
| 83 | 100 | 100 |
| 84 | 100 | 100 |
| 85 | 100 | 98 |
| 86 | 100 | 100 |
| 88 | 100 | 90 |
| 89 | 100 | 100 |
| 90 | 100 | 91 |
| 91 | 100 | 100 |
| 92 | 100 | 100 |
| 93 | 95 | 63 |
| 94 | 100 | 92 |
| 97 | 100 | 100 |
| 98 | 100 | 100 |
| 99 | 100 | 100 |
| 101 | 100 | 100 |
| 103 | 100 | 100 |
| 104 | 100 | 100 |
| *chlordimeform | 100 | 55 |

*Cl—⟨phenyl, CH$_3$⟩—N=C(H)—N(CH$_3$)$_2$

We claim:

1. A compound represented by the formula $$R_1 \cdots N-\overset{Z}{\underset{\|}{C}}NH-R_3 \quad \text{or} \quad R_1 \cdots N-\overset{Z}{\underset{\|}{C}}NH-R_3$$
(with $R_2$, $O$, $Y$ ring substituents)

or racemate thereof wherein
each of Y and Z is oxygen or sulfur,
$R_1$ is alkyl of one to four carbon atoms,
$R_2$ is thienyl, furyl, phenyl, phenyl having one alkoxy, or phenyl having one or two substituents selected from a group consisting of alkyl, halogen, haloalkyl, nitro and methylenedioxy, and
$R_3$ is a five to seven membered cycloalkyl with or without one or two methyl, cyclohexenyl or tetrahydropyranyl.

2. Trans-4-methyl-5-[4-methylphenyl]-3-cyclohexylcarbamoyl-2-oxazolidone of claim 1.

3. Trans-4-methyl-5-[4-methylphenyl]-3-[2-tetrahydropyranylcarbamoyl]-2-oxazolidone of claim 1.

4. Trans-4-methyl-5-[4-trifluoromethylphenyl]-3-cyclohexylcarbamoyl-2-oxazolidone of claim 1.

5. Trans-4-methyl-5-[4-methylphenyl]-3-cyclohexylcarbamoyl-oxazolidine-2-thione of claim 1.

6. Trans-4-methyl-5-[4-methylphenyl]-3-[2-methylcyclohexylcarbamoyl]-2-oxazolidone of claim 1.

7. Trans-4-methyl-5-[4-methylphenyl]-3-[4-methylcyclohexylcarbamoyl]-2-oxazolidone of claim 1.

8. Trans-4-methyl-5-[3,4-methylenedioxyphenyl]-3-[2-tetrahydropyranylcarbamoyl]-2-oxazolidone of claim 1.

9. Trans-4-methyl-5-[4-methylphenyl]-3-[2-tetrahydropyranylcarbamoyl]-oxazolidine-2-thione of claim 1.

10. Trans-4-methyl-5-[4-chlorophenyl]-3-cyclohexylcarbamoyloxazolidine-2-thione of claim 1.

11. Trans-4-methyl-5-[4-chlorophenyl]-3-[2-tetrahydropyranylcarbamoyl]-2-oxazolidone of claim 1.

12. Trans-4-methyl-5-[3,4-methylenedioxyphenyl]-3-[2-methylcyclohexylcarbamoyl]-2-oxazolidone of claim 1.

13. Trans-4-methyl-5-[3,4-dimethylphenyl]-3-[2-methylcyclohexylcarbamoyl]-2-oxazolidone of claim 1.

14. Trans-4-methyl-5-[3,4-dimethylphenyl]-3-cyclohexylcarbamoyl-2-oxazolidone of claim 1.

15. Trans-4-methyl-5-[4-methylphenyl]-3-cyclohexylthiocarbamoyl-2-oxazolidone of claim 1.

* * * * *

UNITED STATES PATENT AND TRADEMARK OFFICE
CERTIFICATE OF CORRECTION

PATENT NO. : 4,431,814

DATED : February 14, 1984

INVENTOR(S) : Isao Iwataki, et al.

It is certified that error appears in the above-identified patent and that said Letters Patent is hereby corrected as shown below:

```
Col. 3 line 59  [1-hydroxy-  ...should read
    --[threo-1-hydroxy- ... --

Col. 4 line 7  [threo-2-hydroxy - should read
    --[threo-1-hydroxy- .. --

Col. 4 line 8  )-2-phenyl] urea   should read
    -- )-2-propyl] urea ...--

Col. 8 between lines 22 and 23 the numbers in
    bracket [152 - 154] should appear below line 23.
```

Signed and Sealed this

Second Day of July 1985

[SEAL]

Attest:

DONALD J. QUIGG

Attesting Officer     Acting Commissioner of Patents and Trademarks